United States Patent
Abbad et al.

(10) Patent No.: US 12,044,121 B2
(45) Date of Patent: Jul. 23, 2024

(54) IN-SITU WETTABILITY MEASUREMENT USING MULTIPLE PARTITIONING TRACERS

(71) Applicant: SAUDI ARABIAN OIL COMPANY, Dhahran (SA)

(72) Inventors: Mohammed Abbad, Dhahran (SA); Muhammad Majid Almajid, Qatif (SA); Hussain Jeshi, Dhahran (SA)

(73) Assignee: SAUDI ARABIAN OIL COMPANY, Dhahran (SA)

(*) Notice: Subject to any disclaimer, the term of this patent is extended or adjusted under 35 U.S.C. 154(b) by 254 days.

(21) Appl. No.: 17/456,320

(22) Filed: Nov. 23, 2021

(65) Prior Publication Data

US 2023/0160298 A1     May 25, 2023

(51) Int. Cl.
| | |
|---|---|
| *E21B 47/11* | (2012.01) |
| *G01N 13/00* | (2006.01) |
| *G01N 15/08* | (2006.01) |
| *G01N 33/24* | (2006.01) |

(52) U.S. Cl.
CPC ............. *E21B 47/11* (2020.05); *G01N 13/00* (2013.01); *G01N 15/0806* (2013.01); *G01N 33/24* (2013.01)

(58) Field of Classification Search
CPC .... E21B 47/11; G01N 13/00; G01N 15/0806; G01N 33/24
See application file for complete search history.

(56) References Cited

U.S. PATENT DOCUMENTS

| | | | | |
|---|---|---|---|---|
| 4,876,449 A | * | 10/1989 | Casad | ................... E21B 47/111 |
| | | | | 250/260 |
| 6,331,436 B1 | * | 12/2001 | Richardson | .......... G01N 33/241 |
| | | | | 436/27 |

(Continued)

FOREIGN PATENT DOCUMENTS

| | | |
|---|---|---|
| BR | 102018012339 A2 | 3/2019 |
| CN | 104730587 A | 6/2015 |

(Continued)

OTHER PUBLICATIONS

Ferreira, "A Single-Well Tracer Test To Estimate Wettability" SPE/DOE; Copyright 1992m Society of Petroleum Engineers Inc. pp. 325-335 (Year: 2019) (Year: 1992).*

(Continued)

*Primary Examiner* — Michael J Dalbo
*Assistant Examiner* — Kaleria Knox
(74) *Attorney, Agent, or Firm* — Osha Bergman Watanabe & Burton LLP

(57) ABSTRACT

A method includes developing a lab-scale representative correlation between wettability index and tracer test return curve data for core samples, obtaining tracer test return curve data for rock at a well of interest, and determining a wettability index of the rock in situ using the representative correlation and the tracer test return curve data for the well. A method includes obtaining core samples of a rock representative of a formation of interest, determining a wettability index of each of the core samples, performing a tracer test on each of the core samples and obtaining tracer return curve data for each of the core samples, building a correlation between the wettability index and the tracer return curve data of the core samples, running a single-well tracer test at a well, obtaining tracer return curve data for the well, and determining a wettability index for the rock of the well.

11 Claims, 4 Drawing Sheets

(56) References Cited

U.S. PATENT DOCUMENTS

| | | |
|---|---|---|
| 10,113,946 B2 | 10/2018 | Wickramathilaka |
| 10,196,555 B2 | 2/2019 | Fathi Najafabadi |
| 10,466,186 B2 | 11/2019 | Kadayam Viswanathan et al. |
| 10,677,706 B2 | 6/2020 | McCarty et al. |
| 2016/0075941 A1 | 3/2016 | Duenckel et al. |
| 2019/0212241 A1 | 7/2019 | Crouse et al. |
| 2019/0381517 A1 | 12/2019 | Thyne |

FOREIGN PATENT DOCUMENTS

| | | | |
|---|---|---|---|
| EP | 2801844 A2 | 11/2014 | |
| WO | WO-2015013697 A1 * | 1/2015 | ............... C09K 8/03 |
| WO | 2020191319 A1 | 9/2020 | |
| WO | 2021076529 A1 | 4/2021 | |

OTHER PUBLICATIONS

Anderson, SPE Conoco Inc., "Wettability Literature Survey—Part 2: Wettability Measurement", pp. 1246-1262 (Year: 1986).*

Hadia "Laboratory investigation on effects of initial wettabilities on performance of law salinity waterflooding", pp. 18-25; Journal of Petroleum Science and Engineering (Year: 2013).*

Ferreira et al.; "A Single-Well Tracer Test To Estimate Wettability", SPE/DOE 24136; Society of Petroleum Engineers; Apr. 22, 1992; pp. 325-335 (11 pages).

Strand et al.; "New wettability test for chalk based on chromatographic separation of SCN- and SO42-", Journal of Petroleum Science and Engineering; vol. 52; Issues 1-4; Jun. 2006; pp. 187-197 (11 pages).

Lejla Tipura, "Wettability Characterization by NMR T2 Measurements in Edwards Limestone", Master Thesis in Reservoir Physics; Universitas Bergensis; 2008 (91 pages).

Alvarez et al.; "Wettability, Oil and Rock Characterization of the Most Important Unconventional Liquid Reservoirs in the United States and the Impact on Oil Recovery", URTEC-2461651-MS; Unconventional Resources Technology Conference; Aug. 1, 2016; pp. 1-21 (21 pages).

Goda et al.; "Wettability Quantification—Prediction of Wettability for Australian Formations", IPTC 15230; International Petroleum Technology Conference; Feb. 7-9, 2012; pp. 1-20 (20 pages).

* cited by examiner

IN-SITU WETTABILITY MEASUREMENT USING MULTIPLE PARTITIONING TRACERS

BACKGROUND

Wettability is a petrophysical phenomenon where one fluid has the tendency to spread and adhere to a solid surface in the presence of another immiscible fluid. In the oilfield industry, the wettability affects the relative permeability of rock to water and oil and, therefore, the displacement process and oil recovery. The general concept of wettability may be illustrated by considering droplets of three different liquids place on a given piece of material, such as glass. A water droplet tends to spread on the glass surface. An oil droplet may spread less than the water droplet and may have almost a hemispherical shape on the glass surface. A droplet of mercury would spread even less than the oil droplet and may have a more spherical shape on the glass surface.

Many multiphase phenomena depend on the wettability character of the rock samples. Specifically, how a fluid or fluids will distribute in a porous media, reservoir rock, is a function of the wettability of a rock sample to fluid(s). A wetting phase is a fluid that preferentially wets a rock surface due to attractive forces and, therefore, the wetting phase is drawn into small pores of the rock. A nonwetting phase is a fluid that does not preferentially wet the rock surface due to repulsive forces and, therefore, the non-wetting phase fill larger pores of the rock. Rocks may be classified as water-wet, oil-wet, or intermediate wettability. In a reservoir, water-wet rock describes rock where the rock or mineral surface is coated with water, and oil and gas occupy the centers of the largest pores. Oil-wet rock describes rock where the rock or mineral surface is coated with oil, and water occupies the centers of the largest pores. A water-wet rock allows water to flow through it much easier than an oil-wet rock. Rock with intermediate wettability has a tendency for both oil and water to adhere to the pore surface of the rock. Due to the heterogeneity present in a reservoir, the wettability of rock samples might vary spectrally. Some areas of the reservoir might exhibit a more water-wet behavior while others might exhibit a more oil-wet behavior. Thus, determining the wettability of the formation is important.

Wettability is currently estimated either by measurement of contact angle or by imbibition test. Both estimation methods require a representative cement/rock sample with filtered oil and synthetic brine. Wettability alteration and process of restoration is a major concern for both methods. In the oilfield industry, wettability alteration is generally the process of making the rock more water-wet. Wettability alteration enhances oil recover in oil-wet or weak water-wet reservoirs; however, wettability alteration inevitably leads to less accurate wettability determination.

The two main methods that are currently used to measure wettability are by determining contact angle, using reservoir fluids and a mineral surface, or by imbibition test on reservoir core plugs with reservoir refined oil and synthetic brine. The results are often affected by wettability alteration due to improper field handling or by not reaching a representative wettability restoration condition in a lab.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to a method including developing a lab-scale representative correlation between wettability index and tracer test return curve data for core samples, obtaining tracer test return curve data for reservoir rock at a well of interest, and determining a wettability index of the reservoir rock in situ using the representative correlation and the tracer test return curve data for the well.

In another aspect, embodiments disclosed herein relate to a method including obtaining core samples of a rock representative of a formation of interest, determining a wettability index of each of the core samples, performing a tracer test on each of the core samples and obtaining tracer return curve data for each of the core samples, building a correlation between the wettability index and the tracer return curve data of the core samples, running a single-well tracer test at a well, obtaining tracer return curve data for reservoir rock of the well, and determining a wettability index for the reservoir rock of the well using the correlation and the tracer return curve data for the well.

In another aspect, embodiments disclosed herein relate to a method of determining wettability characteristics of a reservoir rock including developing a correlation between a wettability index and tracer test return curve data on a lab-scale, obtaining well-scale tracer test return curve data for a reservoir, and predicting the wettability characteristic of the reservoir based on the correlation and the well-scale tracer test return curve data.

Other aspects and advantages of the claimed subject matter will be apparent from the following description and the appended claims.

DETAILED DESCRIPTION

In one aspect, embodiments disclosed herein relate to a method of determining wettability of a reservoir rock. More specifically, embodiments herein relate to a method of determining wettability of a reservoir rock in situ that includes a combination of lab-scaled data measurements and field-scale response of the reservoir to predict field-scale wettability of the reservoir rock.

Embodiments disclosed herein may provide for use of lab data and in situ well data to estimate the wettability behavior of reservoir rock surrounding a wellbore area at reservoir temperature and pressure, which may further provide more accurate production forecasts and better recovery estimates. In accordance with one or more embodiments, a method of determining wettability of a reservoir rock includes developing a representative correlation between a wettability index and tracer test return curve data analysis at a lab scale, obtaining well-scale return curve data for a reservoir, and predicting the wettability characteristic of the reservoir based on the representative correlation and the well-scale return curve data.

In another aspect, embodiments disclosed herein relate to a method of determining wettability index of a reservoir rock that includes developing a lab-scale representative correlation between wettability index and tracer return curve data, conducting a single-well tracer test in situ to obtain return curve data for the well, and using the return curve data for the well in the developed lab-scale representative correlation to predict the wettability index of the reservoir rock.

In another aspect, embodiments disclosed herein relate to a method of determining a wettability index of a reservoir rock in situ that includes obtaining core samples of a rock representative of a formation of interest, determining a wettability index of each of the core samples, performing a tracer test on each of the core samples and obtaining tracer return curve data for each of the core samples, building a correlation between the wettability index and the tracer return curve data, running a single-well tracer test at a well, obtaining tracer return curve data for the well, and determining a wettability index for the reservoir rock of the well using the correlation and the tracer return curve data for the well.

Figure 1:
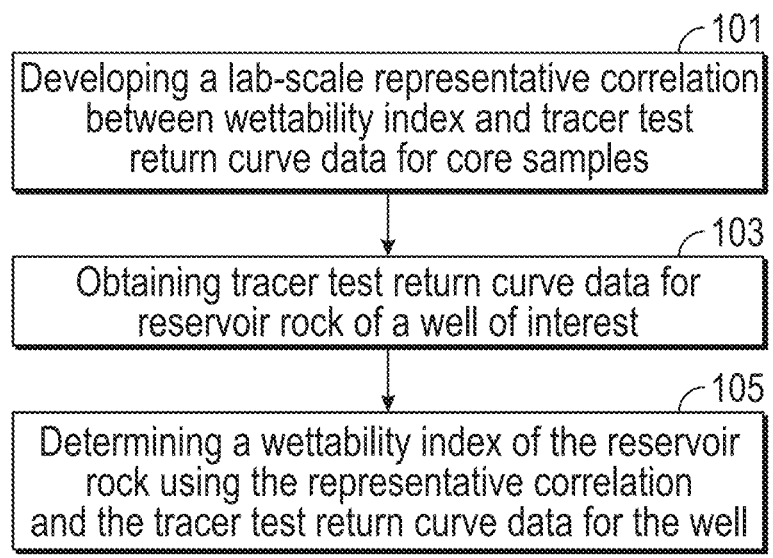
FIG. 1 is an overview of a methodology for determining in situ wettability index of a reservoir rock in accordance with one or more embodiments disclosed herein.

Referring to FIG. 1 shows an overview of a methodology for determining in situ wettability index of a reservoir rock in accordance with one or more embodiments disclosed herein. As shown, the method includes developing a lab-scale representative correlation between wettability index and tracer test return curve data for core samples, shown at 101, obtaining tracer test return curve data for reservoir rock at a well of interest, shown at 103, and determining a wettability index of the reservoir rock using the representative correlation and the tracer test return curve data for the well, shown at 105.

Figure 2:
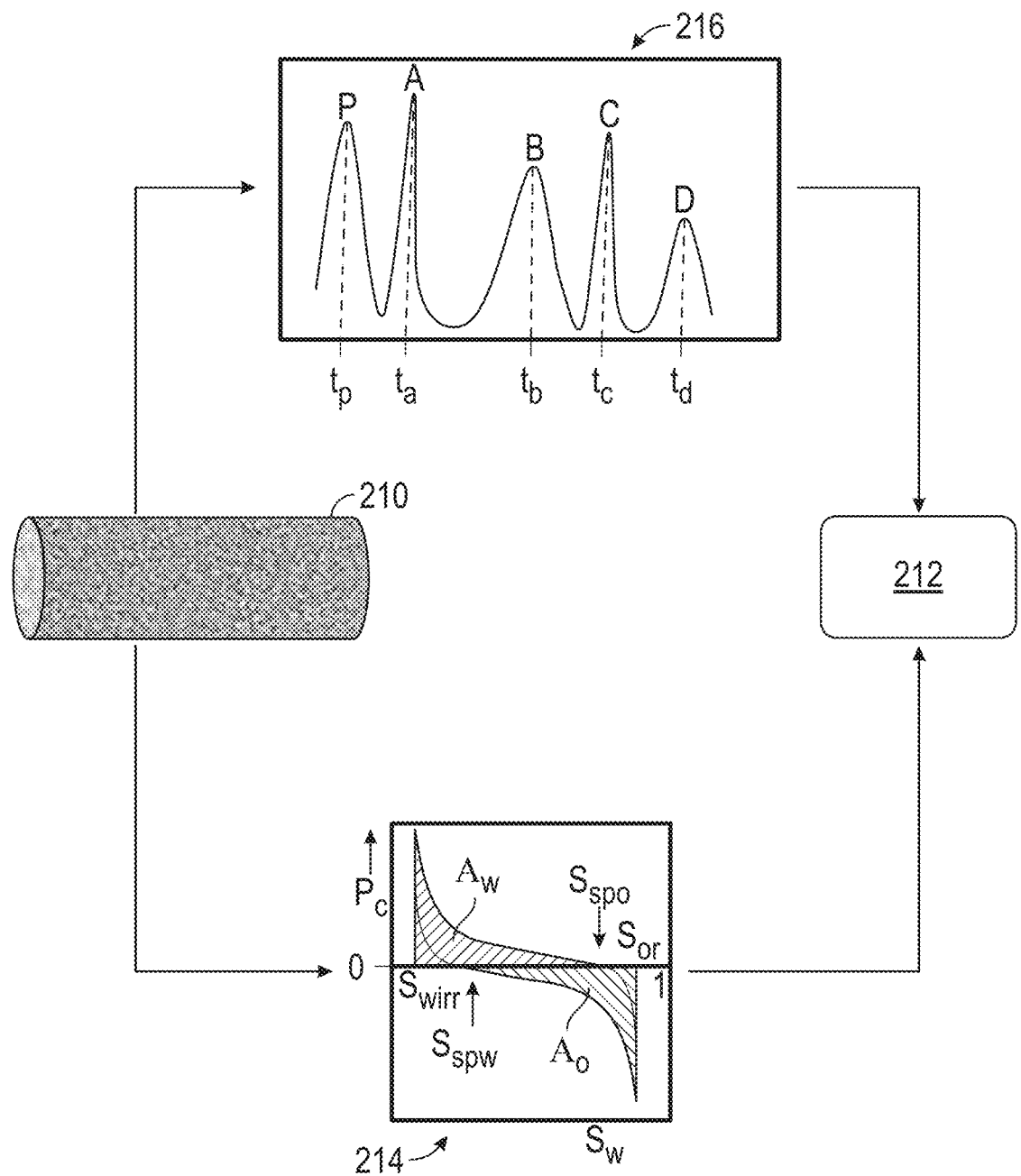
FIG. 2 is a schematic of a step of developing a lab-scale representative correlation in accordance with embodiments disclosed herein.

Developing a lab-scale representative correlation between wettability index and tracer test return curve data for core samples, shown at 101, builds a relationship between the wettability indexes of multiple core samples and tracer return curve data of the multiple core samples obtained through two different procedures. Specifically, referring to FIG. 2, in which a schematic of the step of developing a lab-scale representative correlation is shown, core samples 210 may be processed according to two different experimental procedures to obtain or build the representative correlation 212. For example, as shown in FIG. 2, for each core sample, two experimental procedures may be performed: (1) an Amott test 214; and (2) a tracer test 216.

Core samples 210 may be sections (generally cylindrical in shape) of a formation on which laboratory analyses may be performed to obtain representative results expected in the formation or well. Additionally, the core samples should be selected such that the core samples generally encompass the range of wettability behavior expected in formation or well of interest. In one embodiment, two or more core samples may be used. In accordance with embodiments disclosed herein, five core samples may be used, as shown and explained with reference to FIG. 2. However, a person of ordinary skill in the art will appreciate that fewer or more core samples may be used without departing from the scope of the present application. The core samples may be from the same field where the method disclosed herein will be used to determine a wettability index of a reservoir rock in situ.

In accordance with embodiments disclosed herein, an Amott test 214 is performed on each of the five samples to determine an Amott index (AI) for each core sample. An Amott test is used to determine a wettability index of a core sample based on a combination of spontaneous imbibition and forced displacement of fluids (oil, water, brine). The Amott test does not provide an absolute measurement; however it is an industry standard for comparing the wettability of various core plugs. Using the Amott test, four basis measurements are obtained: (1) the amount of water or brine spontaneously imbibed by the core sample; (2) the amount of water or brine forcibly imbibed by the core sample; (3) the amount of oil spontaneously imbibed by the core sample; and (4) the amount of oil forcibly imbibed by the core sample.

A spontaneous measurement may be performed by placing the core sample in a container with a known volume of a fluid to be imbibed (e.g., a water or brine) such that the core sample is completely submerged and measuring the volume of the fluid displaced by the imbibing fluid (e.g., oil). A forced measurement may be performed by flowing the imbibing fluid through the core sample and measuring the amount of the fluid displaced. Alternatively, a centrifuge may be used and the amount of fluid displaced measured. It is worth nothing that water-wet samples only spontaneously imbibe water and oil-wet samples only spontaneously imbibe oil. Core samples that do not spontaneously imbibe oil or water are neutrally-wet. The Amott test 214 in FIG. 2 shows the general plot curve for wettability test data using the Amott test method.

After the test data is obtained, two ratios are determined: displacement by oil ratio and displacement by water ratio. The wettability ratios or index for water ($I_w$) and oil ($I_o$) are the ratios of the spontaneous imbibition of the fluid to the total imbibition of each fluid, as shown in Equations (1) and (2) below, wherein $S_{spw}$ is spontaneous water saturation, $S_{wirr}$ is irreducible water saturation, $S_{or}$ is residual oil saturation, and $S_{spo}$ is spontaneous oil saturation. The Amott test then provides for the Amott-Harvey wettability index to be determined as the difference between the water-wetting index ($I_w$) and the oil-wetting index ($I_o$), as shown in Equation (1) below:

$$I_w = \frac{S_{spw} - S_{wirr}}{1 - S_{wirr} - S_{or}} \quad (1)$$

$$I_o = \frac{S_{sp0} - S_{or}}{1 - S_{wirr} - S_{or}} \quad (2)$$

$$AI = I_w - I_o \quad (3)$$

The Amott test results in an Amott-Harvey index results in a number ranging from −1 to 1. A rock having a Amott-Harvey index of 0.3-1 is defined as water wet; an index of 0-0.3 is defined as weakly water wet; an index of −0.3-0 is defined as weakly oil wet; and an index of −1-0.3 is defined as oil wet. The above process is repeated for each core sample, such that each core sample has a representative Amott indexes (AI).

Referring back to FIG. 2, a tracer test 216 for each of the core samples is also preformed to obtain return curve data for each of the core samples. Partitioning tracer tests may be used to estimate residual oil saturation. Specifically, in using different tracers, the difference in arrival times between tracers may be used to estimate the volume of oil remaining in a rock after the tracer test. A partitioning tracer test includes a passive or conservative tracer and multiple partitioning tracers.

As shown in FIG. 2, a tracer test 216, such as a partitioning tracer test, is performed on each core sample to obtain return curve data (as shown) for the tracers. To perform the tracer test, each core sample is coreflooded or injected with, for example, for example, five different tracers. One of ordinary skill in the art will appreciate that various different tracers may be used to perform the partitioning tracer test. Examples of passive tracers include isopropanol and methanol. Partitioning tracers used in the oilfield are often used in single well chemical tracer tests (SWCTT) for residual saturation measurements. Examples of partitioning tracers include ethanol or more complex derivatives of stable fluorinated benzoic acids (FBAs). Other examples of partitioning tracers include two substituents on the aromatic ring, either one fluorine (F) and on trifluoromethyl group (CF3) or one fluorine (F) and one chlorine (Cl), for example, fluorobenzyl alcohol and 3,4-difluorobenzyl alcohol. One of ordinary skill in the art will appreciate that fewer or more tracers may be used without departing from the scope of embodiments disclosed herein. In the example with five tracers, each of the tracers is a different compound or chemical, with one passive or conservative tracer and four partitioning tracers. The example plot curve in FIG. 2 is representative of return curve data obtained from the tracer test 216, with retention time on the x-axis and tracer concentration (ppm) on the y-axis. As indicated in the example plot curve in FIG. 2, the partitioning tracers A, B, C, and D have a retention time in the core sample that is longer relative to the passive tracer P. The retention time of the partitioning tracers is longer than the passive tracer P because the partitioning tracers partition into other phases(s) that are present. Several partitioning tracers are used to span a wider range of partition coefficients.

After the core samples have been tested using the Amott test and the tracer test, as described above with reference to FIG. 2, there is one wettability (Amott-Harvey) index and five time values (based on the return curve generated from the tracer test) associated with each core sample. By obtaining the wettability index of multiple core samples, a range of representative wettability index and return curve behavior of the reservoir of interest is provided. A representative correlation between the two experimental procedures (Amott test and tracer test) may then be built.

The correlation between the two experimental procedures may be achieved using various methods. In one or more embodiments, the correlation may be obtained by constructing a system of linear equations for the various core samples with now known and different wettability indexes. The system can be summarized by the following equations:

$$A\vec{t} = \vec{I} \quad (4)$$

$$\begin{bmatrix} a_1 & b_1 & c_1 & d_1 \\ a_2 & b_2 & c_2 & d_2 \\ a_3 & b_3 & c_3 & d_3 \\ a_4 & b_4 & c_4 & d_4 \end{bmatrix} \begin{bmatrix} t_a/t_p \\ t_b/t_p \\ t_c/t_p \\ t_d/t_p \end{bmatrix} = \begin{bmatrix} WI_1 \\ WI_2 \\ WI_3 \\ WI_4 \end{bmatrix} \quad (5)$$

where t represents the retention time of the partitioning tracers A, B, C, D with respect to the retention time of the passive tracer P, and I is the wettability index (WI) for each of the core samples (1, 2, 3, 4) determined using the Amott test. Matrix A, therefore, represents the correlation (212 in FIG. 2) between the return curve data, namely, time t, for each tracer (a, b, c, d relative to passive tracer p) and the wettability index of the reservoir rock to be solved. One the correlation (matrix A) has been built or determined, the wettability index of a reservoir rock in the field of interest can then be predicted by finding well-scale return curve data for a given reservoir rock.

In one or more embodiments, the correlation between the two experimental procedures (Amott test and tracer test) may be built through artificial intelligence or finite element fluid flow simulation modeling on a computer. Using artificial intelligence, a neural network may be built, and trained using data about the reservoir rock, core samples, and wettability behavior to output the correlation. Using fluid flow simulation modeling, a physical description of mass and transport equations may be solved given input of the core samples to determine the correlation.

The well-scale return curve data for a given reservoir rock may be obtained through various methods. In accordance with one or more embodiments, the return curve data may be obtained using a single-well tracer test conducted at the well of interest. The single-well tracer test includes injection of a reservoir with a passive tracer P and multiple partitioning tracers (e.g., A, B, C, D). The well is then shut-in for a period of time. The well is then produced and tracer data, water cuts, and bottomhole pressures may be recorded. Different wettabilities of the rock formations provoke different and characteristic behavior during injection, shut in, and production periods, because wetting condition of the rock formation affects the transport properties of the reservoir. Reservoir rock with different wettabilities also have different fractional flow characteristics. Thus, tracers have different velocities and breakthrough times. The breakthrough times or retention times, as shown in the plot in FIG. 3, of the tracers used in the single-well tracer test therefore provide information indicative of the wettability of the rock.

Figure 3:
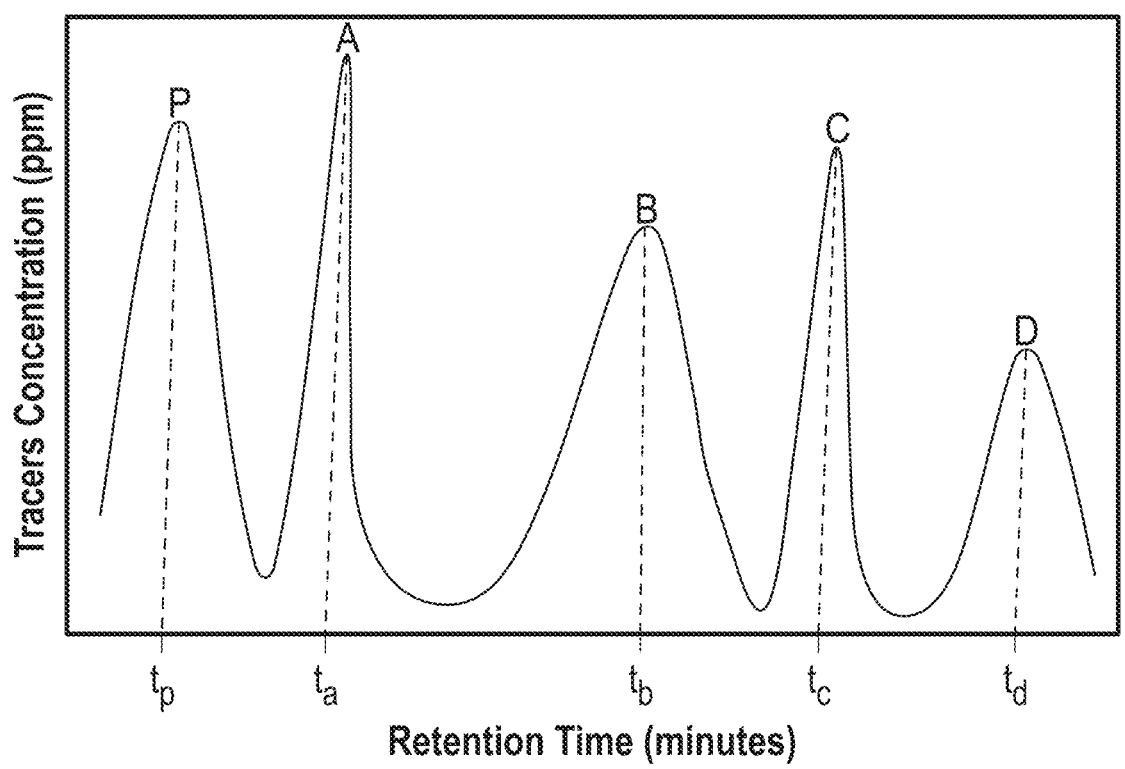
FIG. 3 is an example plot curve representative of return curve data obtained from a single-well tracer test in accordance with embodiments disclosed herein.

FIG. 3 shows an example plot curve representative of return curve data obtained from a single-well tracer test, with retention time on the x-axis and tracer concentration (ppm) on the y-axis. As indicated in the example plot curve in FIG. 3, the partitioning tracers A, B, C, and D have a retention time in the reservoir rock that is longer relative to the passive tracer P. As discussed above, the retention time of the partitioning tracers is longer than the passive tracer P because the partitioning tracers partition into other phases(s) that are present. Several partitioning tracers are used to span a wider range of partition coefficients.

The return curve data, namely the retention time t of the different partitioning tracers A, B, C, D, may then be plugged or entered back into the correlation built from the lab-scale wettability and return curve data. For example, the retention times t in FIG. 3 determined from the single-well tracer test may be plugged back into the system of linear equations, shown at Equation 5, along with the developed correlation matrix A determined from the lab-scale Amott and tracer tests, to predict the wettability index (WI) for the reservoir rock of the reservoir near the wellbore of interest at reservoir temperatures and pressures. Once the correlation has been built for a particular well, formation, or field of interest, the method of building the correlation does not need to be repeated. The correlation may be reused with new single-well tracer tests to determine, update, or estimate the wettability of reservoir rock in that field.

Figure 4:
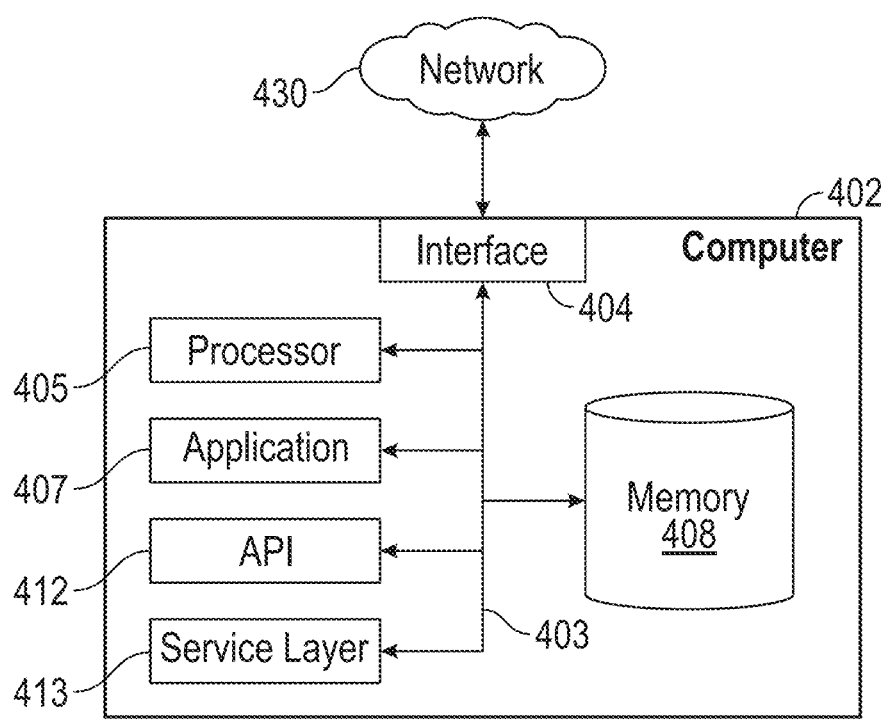
FIG. 4 shows a computing device in accordance with one or more embodiments.

Embodiments disclosed herein may be implemented on a computing device, such as the one shown in FIG. 4. FIG. 4 is a block diagram of a computer system 402 used to provide computational functionalities associated with described algorithms, methods, functions, processes, flows, and procedures as described in the instant disclosure, according to an implementation. The illustrated computer 402 is intended to encompass any computing device such as a high performance computing (HPC) device, a server, desktop computer, laptop/notebook computer, wireless data port, smart phone, personal data assistant (PDA), tablet computing device, one or more processors within these devices, or any other suitable processing device, including both physical or virtual instances (or both) of the computing device. Additionally, the computer 402 may include a computer that includes an input device, such as a keypad, keyboard, touch screen, or other device that can accept user information, and an output device that conveys information associated with the operation of the computer 402, including digital data, visual, or audio information (or a combination of information), or a GUI.

The computer 402 can serve in a role as a client, network component, a server, a database or other persistency, or any other component (or a combination of roles) of a computer system for performing the subject matter described in the instant disclosure. The illustrated computer 402 is communicably coupled with a network 430. In some implementations, one or more components of the computer 402 may be configured to operate within environments, including cloud-computing-based, local, global, or other environment (or a combination of environments).

At a high level, the computer 402 is an electronic computing device operable to receive, transmit, process, store, or manage data and information associated with the described subject matter. According to some implementations, the computer 402 may also include or be communicably coupled with an application server, e-mail server, web server, caching server, streaming data server, business intelligence (BI) server, or other server (or a combination of servers).

The computer 402 can receive requests over network 430 from a client application (for example, executing on another computer 402) and responding to the received requests by processing the said requests in an appropriate software application. In addition, requests may also be sent to the computer 402 from internal users (for example, from a command console or by other appropriate access method), external or third-parties, other automated applications, as well as any other appropriate entities, individuals, systems, or computers.

Each of the components of the computer 402 can communicate using a system bus 403. In some implementations, any or all of the components of the computer 402, both hardware or software (or a combination of hardware and software), may interface with each other or the interface 404 (or a combination of both) over the system bus 403 using an application programming interface (API) 412 or a service layer 413 (or a combination of the API 412 and service layer 413. The API 412 may include specifications for routines, data structures, and object classes. The API 412 may be either computer-language independent or dependent and refer to a complete interface, a single function, or even a set of APIs. The service layer 413 provides software services to the computer 402 or other components (whether or not illustrated) that are communicably coupled to the computer 402. The functionality of the computer 402 may be accessible for all service consumers using this service layer. Software services, such as those provided by the service layer 413, provide reusable, defined business functionalities through a defined interface. For example, the interface may be software written in JAVA, C++, or other suitable language providing data in extensible markup language (XML) format or other suitable format. While illustrated as an integrated component of the computer 402, alternative implementations may illustrate the API 412 or the service layer 413 as stand-alone components in relation to other components of the computer 402 or other components (whether or not illustrated) that are communicably coupled to the computer 402. Moreover, any or all parts of the API 412 or the service layer 413 may be implemented as child or sub-modules of another software module, enterprise application, or hardware module without departing from the scope of this disclosure.

The computer 402 includes an interface 404. Although illustrated as a single interface 404 in FIG. 4, two or more interfaces 404 may be used according to particular needs, desires, or particular implementations of the computer 402. The interface 404 is used by the computer 402 for communicating with other systems in a distributed environment that are connected to the network 430. Generally, the interface 404 includes logic encoded in software or hardware (or a combination of software and hardware) and operable to communicate with the network 430. More specifically, the interface 404 may include software supporting one or more communication protocols associated with communications such that the network 430 or interface's hardware is operable to communicate physical signals within and outside of the illustrated computer 402.

The computer 402 includes at least one computer processor 405. Although illustrated as a single computer processor 405 in FIG. 4, two or more processors may be used according to particular needs, desires, or particular implementations of the computer 402. Generally, the computer processor 405 executes instructions and manipulates data to perform the operations of the computer 402 and any algorithms, methods, functions, processes, flows, and procedures as described in the instant disclosure.

The computer 402 also includes a memory 408 that holds data for the computer 402 or other components (or a combination of both) that can be connected to the network 430. For example, memory 408 can be a database storing data consistent with this disclosure. Although illustrated as a single memory 408 in FIG. 4, two or more memories may be used according to particular needs, desires, or particular implementations of the computer 402 and the described functionality. While memory 408 is illustrated as an integral component of the computer 402, in alternative implementations, memory 408 can be external to the computer 402.

The application 407 is an algorithmic software engine providing functionality according to particular needs, desires, or particular implementations of the computer 402, particularly with respect to functionality described in this disclosure. For example, application 407 can serve as one or more components, modules, applications, etc. Further, although illustrated as a single application 407, the application 407 may be implemented as multiple applications 407 on the computer 402. In addition, although illustrated as integral to the computer 402, in alternative implementations, the application 407 can be external to the computer 402.

There may be any number of computers 402 associated with, or external to, a computer system containing computer 402, each computer 402 communicating over network 430. Further, the term "client," "user," and other appropriate terminology may be used interchangeably as appropriate without departing from the scope of this disclosure. Moreover, this disclosure contemplates that many users may use one computer 402, or that one user may use multiple computers 402.

In some embodiments, the computer 402 is implemented as part of a cloud computing system. For example, a cloud computing system may include one or more remote servers along with various other cloud components, such as cloud storage units and edge servers. In particular, a cloud computing system may perform one or more computing operations without direct active management by a user device or local computer system. As such, a cloud computing system may have different functions distributed over multiple locations from a central server, which may be performed using one or more Internet connections. More specifically, cloud computing system may operate according to one or more service models, such as infrastructure as a service (IaaS), platform as a service (PaaS), software as a service (SaaS), mobile "backend" as a service (MBaaS), serverless computing, artificial intelligence (AI) as a service (AIaaS), and/or function as a service (FaaS). Embodiments disclosed herein advantageously provides a method for correlating Amott-Harvey wettability index (−1 to 1) to multiple known core samples with various fluid systems and various wettability indexes and creating a system of equations that describes the results with generated tracers curve data. The method also includes using the obtained results to solve for an in-situ rock/fluid system around the wellbore at a residual oil saturation condition. This proposed test may be a single-well tracer test while measuring residual oil saturation. Thus, both residual oil saturation and wettability index can be measured directly from this test. Determining the wettability index in situ in accordance with embodiments disclosed herein advantageously provides a method without the use of any numerical simulations or correlations. A method in accordance with embodiments disclosed herein may also provide another level of more definitive wettability evaluation by measuring wettability in situ around the wellbore using multiple partitioning tracers. Furthermore, embodiments disclosed herein also advantageously provide a method for predicting wettability behavior of the reservoir rock surrounding the wellbore area at reservoir temperature and pressure.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112(f) for any limitations of any of the claims herein, except for those in which the claim expressly uses the words 'means for' together with an associated function.

What is claimed:

1. A method, comprising:
   obtaining core samples of a rock representative of a formation of interest;
   developing a lab-scale representative correlation between wettability index and tracer test return curve data for the core samples,
   wherein developing the lab-scale representative correlation comprises constructing a system of linear equations and performing an Amott test on each of the core samples to determine the wettability index of each of the core samples;
   obtaining tracer test return curve data for reservoir rock at a well of interest,
   wherein the obtaining tracer test return curve data for reservoir rock at the well of interest comprises injecting a reservoir with a plurality of tracers and determining a retention time for each tracer from the tracer test return curve data for the reservoir rock; and
   determining a wettability index of the reservoir rock in situ using the representative correlation and the tracer test return curve data for the well,
   wherein the determining the wettability index of the reservoir rock comprises entering the retention time for each tracer of the reservoir rock and the representative correlation into the system of linear equations.

2. The method of claim 1, wherein the developing the lab-scale representative correlation further comprises performing a tracer test on each of the core samples.

3. The method of claim 2, wherein the performing the tracer test comprises injecting five tracers into each of the core samples and obtaining the tracer test return curve data for each of the core samples.

4. The method of claim 3, wherein four of the five tracers are partitioning tracers.

5. A method, comprising:
   obtaining core samples of a rock representative of a formation of interest;
   determining a wettability index of each of the core samples;
   performing a tracer test on each of the core samples and obtaining tracer return curve data for each of the core samples;
   building a correlation between the wettability index and the tracer return curve data of the core samples;
   wherein building the correlation comprises solving a system of linear equations $A\vec{t}=\vec{I}$ for A, wherein A is the correlation, t is a retention time of the tracers in the core samples, and I is the wettability index of the core samples;
   running a single-well tracer test at a well;
   obtaining tracer return curve data for reservoir rock of the well; and
   determining a wettability index for the reservoir rock of the well using the correlation and the tracer return curve data for the well.

6. The method of claim 5, wherein the determining the wettability index of each of the core samples comprises performing an Amott test.

7. The method of claim 5, wherein the performing a tracer test on each of the core samples comprises injecting each of the core samples with a plurality of tracers.

8. The method of claim 5, wherein the tracer return curve data for the core samples comprises a retention time for each of the tracers for each of the core samples.

9. The method of claim 5, wherein obtaining tracer return curve data for reservoir rock of the well comprises injecting a plurality of tracers into the reservoir rock and determining a retention time of each of the plurality of tracers injected into the reservoir rock.

10. The method of claim 9, wherein determining a wettability index for the reservoir rock of the well comprises using the correlation A and the retention time of each of the plurality of tracers injected into the reservoir rock as t to solve $A\vec{t}=\vec{I}$ for I.

11. The method of claim 9, wherein the retention time of the plurality of tracers is a retention time of partitioning tracers relative to a passive tracer.

* * * * *